(12) United States Patent
Mahó et al.

(10) Patent No.: US 9,683,010 B2
(45) Date of Patent: Jun. 20, 2017

(54) PROCESS FOR THE PRODUCTION OF 21-METHOXY-11-BETA-PHENYL-19-NOR-PREGNA-4,9-DIENE-3,20-DIONE DERIVATIVES

(71) Applicant: RICHTER GEDEON NYRT., Budapest (HU)

(72) Inventors: Sándor Mahó, Budapest (HU); Csaba Sánta, Budapest (HU); János Csörgei, Budapest (HU); Gábor Szabó, Dorog (HU); Tamás Schäfer, Budapest (HU); Zoltán Béni, Maglód (HU)

(73) Assignee: Richter Gedeon Nyrt., Budapest (HU)

( * ) Notice: Subject to any disclaimer, the term of this patent is extended or adjusted under 35 U.S.C. 154(b) by 0 days.

(21) Appl. No.: 15/108,026

(22) PCT Filed: Feb. 16, 2015

(86) PCT No.: PCT/IB2015/051124
§ 371 (c)(1),
(2) Date: Jun. 24, 2016

(87) PCT Pub. No.: WO2015/121840
PCT Pub. Date: Aug. 20, 2015

(65) Prior Publication Data
US 2016/0326211 A1 Nov. 10, 2016

(30) Foreign Application Priority Data
Feb. 17, 2014 (HU) ..................................... 1400080

(51) Int. Cl.
| | | |
|---|---|---|
| *C07J 5/00* | (2006.01) | |
| *C07J 3/00* | (2006.01) | |
| *C07J 41/00* | (2006.01) | |
| *C07J 51/00* | (2006.01) | |

(52) U.S. Cl.
CPC ......... *C07J 41/0083* (2013.01); *C07J 5/0053* (2013.01); *C07J 51/00* (2013.01)

(58) Field of Classification Search
CPC ..................................... C07J 5/00; C07J 3/00
USPC ...................................... 540/34, 36; 552/598
See application file for complete search history.

(56) References Cited

U.S. PATENT DOCUMENTS

| | | |
|---|---|---|
| 6,900,193 B1 | 5/2005 | Kim et al. |
| 2003/0060646 A1 | 3/2003 | Kim et al. |
| 2010/0113408 A1 | 5/2010 | Kim et al. |
| 2010/0137622 A1 | 6/2010 | Bódi et al. |

OTHER PUBLICATIONS

Stork et al.: "The Total Synthesis of a Natural Cardenolide: (+)-Digitoxigenin", J. Am. Chem. Soc., 1996, vol. 118, No. 43, pp. 10660-10661 and supplemental pp. 1-17.
Yamato et al.: "Chemical Structure and Sweet Taste of Isocoumarin and Related Compounds.", Chem. Pharm. Bull., 1977, vol. 25, No. 4, pp. 700-705.

*Primary Examiner* — Brenda Coleman
(74) *Attorney, Agent, or Firm* — Jason D. Voight

(57) ABSTRACT

The present invention relates to a process for the synthesis of compounds of formula (I),

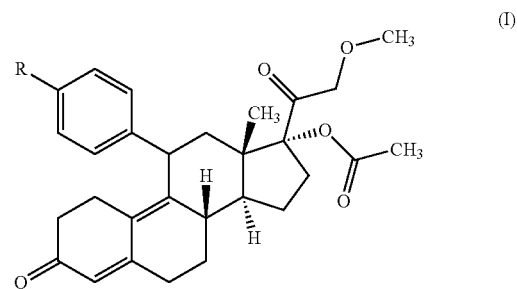

wherein the meaning of R is dimethylamino or acetyl group, using the compound of formula (III) or (IV), wherein the meaning of R' is dimethylamino or 2-methyl-1,3-dioxan-2-yl group, as starting material and methoxymethyl lithium as reagent.

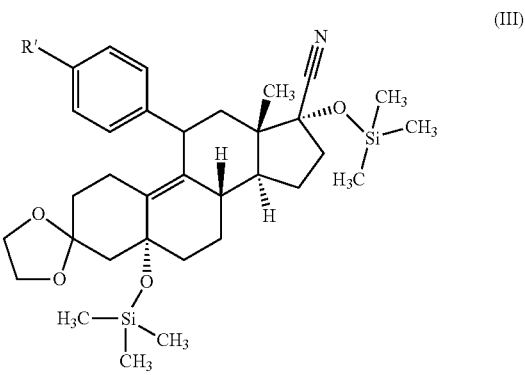

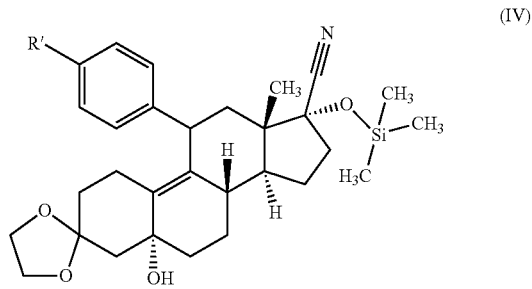

9 Claims, No Drawings

PROCESS FOR THE PRODUCTION OF 21-METHOXY-11-BETA-PHENYL-19-NOR-PREGNA-4,9-DIENE-3,20-DIONE DERIVATIVES

This is the national stage of International Application PCT/IB2015/051125, filed Feb. 16, 2015.

FIELD OF THE INVENTION

The present invention relates to a new process for the synthesis of 21-methoxy-pregnane derivatives of formula (I),

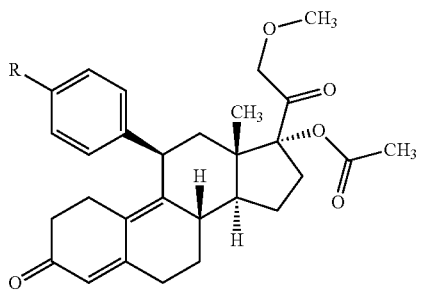

wherein the meaning of R is dimethylamino or acetyl group, using methoxymethyl lithium reagent,
as well as to the intermediate of formula (III), wherein the meaning of R' is 2-methyl-1,3-dioxan-2-yl group.

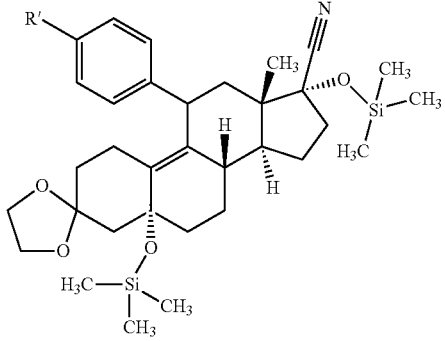

BACKGROUND OF THE INVENTION

21-Alkoxy-pregnane compounds possessing significant antiprogestogen activity were first described in the patent applications No. WO97041145 and WO01074840. Telapristone acetate (CDB-4124) is this type of compound, which is currently under clinical development in Phase III studies. According to the results published so far it is exceptionally promising for the treatment of uterine fibroma (a benign tumor of connective tissue).

The synthesis of 21-methoxy-pregnane derivatives of formula (I) was first described in the patent application No. WO97041145 (see Figure 1.).

The synthesis of compound of formula (I) (R=dimethylamino group) was carried out the following way:

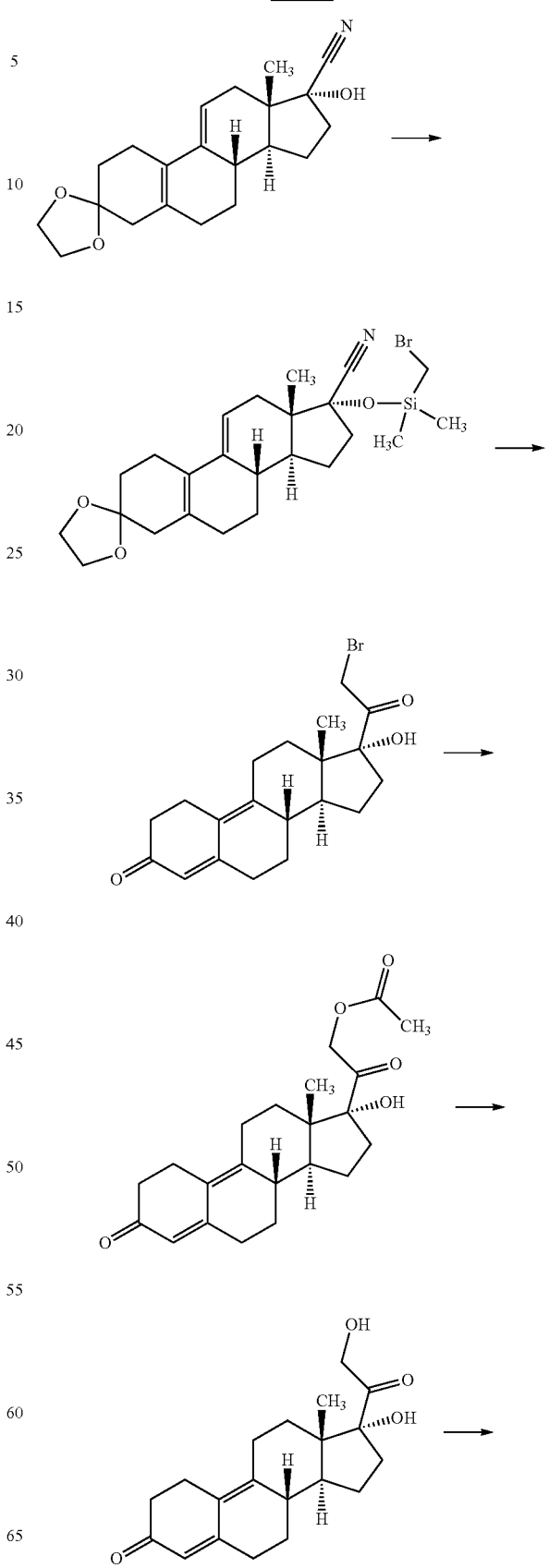

Figure 1.

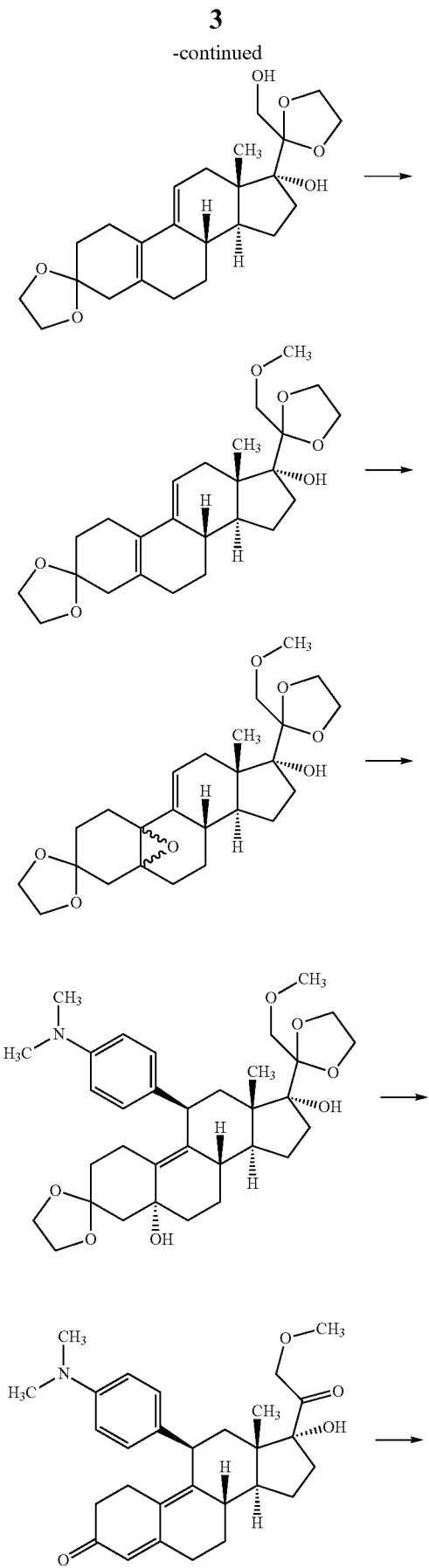

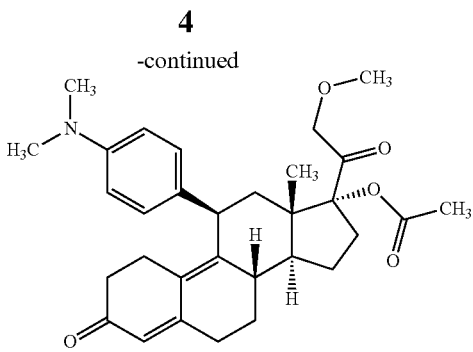

First the side-chain in position 17 was introduced, then the obtained compound was substituted in position 11 by Grignard reaction.

The hydroxyl group in position 17 of the commercially available 3,3-[1,2-ethanediyl-bis-(oxy)]-17α-hydroxy-estr-5(10),9(11)-dien-17β-carbonitrile was silylated with (bromomethyl)dimethylsilyl chloride. Then the 17-silyloxy bromo compound was transformed into 21-bromo compound using lithium diisopropylamide at −78° C. Introduction of the methoxy group in position 21 was carried out in a rather complicated, multistep process: via the 21-acetoxy and 21-hydroxy derivatives, using 6 equivalent excess of trimethyloxonium tetrafluoroborate salt together with proton sponge (SNAP reaction). On one hand this method is expensive, on the other hand the removal of the proton sponge is difficult, in many cases it requires the purification of the product in several steps.

Further disadvantage of the process is that the epoxide needed for the Grignard reaction is synthesized in the 7th step. This is not economical, because during the epoxide formation four isomers of the epoxide are formed according to NMR spectroscopy.

The synthesis, which is identical with the above mentioned one, of compound of formula (I) (R=acetyl) is described in the patent application No. WO01074840.

A partly different synthesis is described in the patent application No. WO01047945. In this case also the side-chain in position 17 was formed, then the substituent in position 11 was introduced by Grignard reaction. In this process the synthesis of the epoxide was also carried out in the advanced phase of the reaction sequence. Introduction of the methoxy group in position 21 was carried out as described in the previous patent applications.

An industrial process is described in the patent application No. WO2009001148 (Figure 2.). The difference between this process and the previously described ones is that first the substituent in position 11 was introduced, then the side-chain in position 17 was formed. The advantage of this process is that the epoxide formation is carried out at the beginning of the reaction sequence, this results in less loss of material as compared to the previously described ones. During the formation of the side-chain in position 17 the carbonitrile was transformed into carbaldehyde by reduction. The obtained carbaldehyde was methoxymethylated in Grignard reaction. Then the oxidation of the hydroxyl group in position 20 was carried out to yield the compound of formula (II), which was acylated. Introduction of the methoxy group was carried out in less steps as compared to the previously described processes, but during the Grignard reaction a mercury compound was used, which is not easily manageable from the point of environmental protection.

Figure 2.

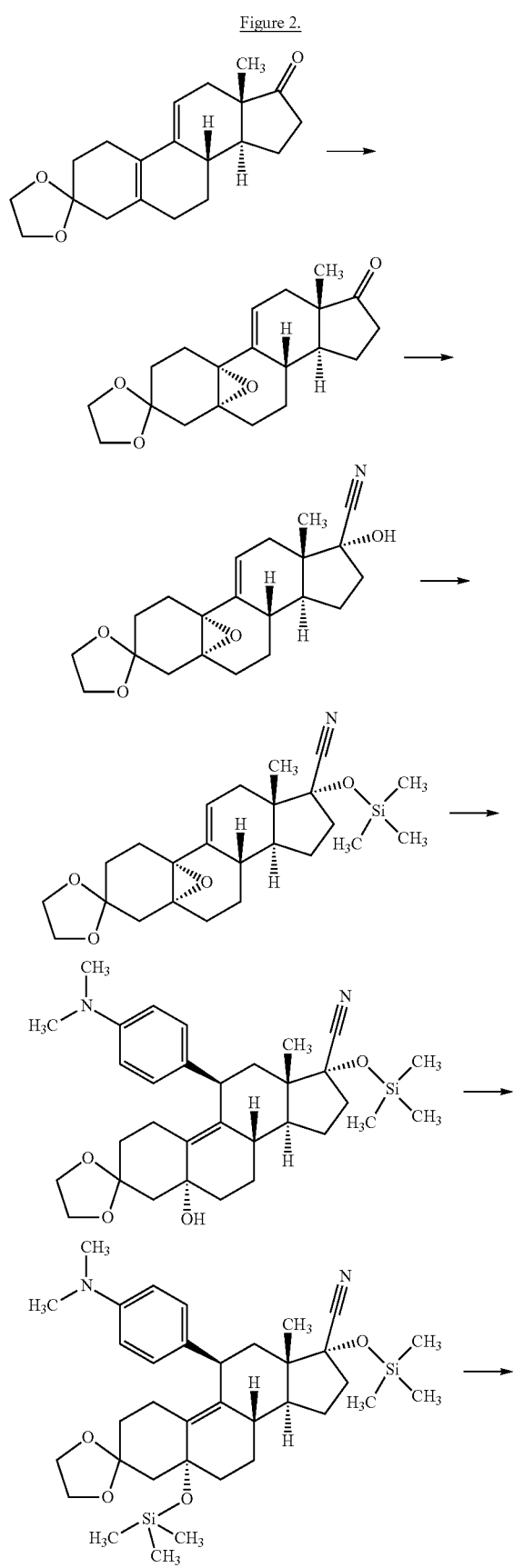
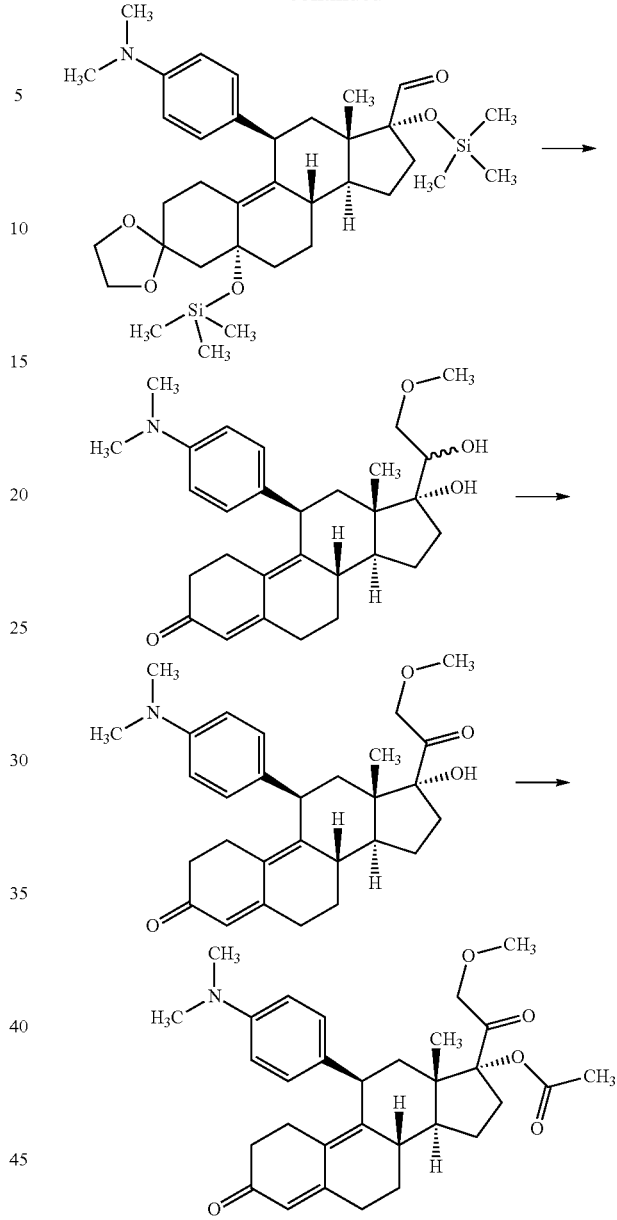

The synthesis of methoxymethyl lithium reagent was first described in 1964 in a publication (Tetrahedron Letters (1964), 24, 1503-6). Lithium was reacted with methoxymethyl chloride in methylal at (−25)-(−30)° C. The so obtained solution of the reagent was reacted with carbonyl group containing compounds (ketones, aldehydes and carboxylic acid esters) and this way alcohols containing methoxymethyl group were synthesized.

Similar process was described in 1967 (Liebigs Ann. Chem. 704, 120-125 (1967)). According to this publication the reagent was used in similar reactions.

In 1996 a process was described in a publication (Tetrahedron 52(5), 1643-1650, (1996)) for the in situ synthesis of ethoxymethyl lithium from chloromethyl ethyl ether and lithium in the presence of 4,4'-di-tert-butylbiphenyl catalyst in tetrahydrofuran at −90° C., which was reacted with compounds containing carbonyl group or with benzonitrile.

Alkoxymethyl lithium reagent has not been used so far in the synthesis of steroids.

SUMMARY OF THE INVENTION

The present invention relates to a new process for the synthesis of 21-methoxy-pregnane derivatives of formula (I), which has less steps as the known ones described above, it is industrially realizable, safe and economical. The process differs from the one described in the patent application No. WO2009001148, that the introduction of the side-chain in position 17 was carried out in a different way, with special regard to the introduction of the methoxy group in position 21. Surprisingly it was found, that introduction of the methoxy group can be carried out in a more simple way, in less steps than in the processes described above, if the compounds of formula (III) or (IV) are reacted with methoxymethyl lithium—synthesized preferably in situ—under proper conditions. In the next step the protective groups of the obtained intermediate were removed by acid hydrolysis and dehydration, than the hydroxyl group in position 17 was acylated. This way the compound of formula (I) was obtained in a more simple, faster and more economical process as compared to the processes described earlier.

The present invention also relates to the intermediate of formula (III), wherein the meaning of R' is 2-methyl-1,3-dioxolan-2-yl group.

DETAILED DESCRIPTION OF THE INVENTION

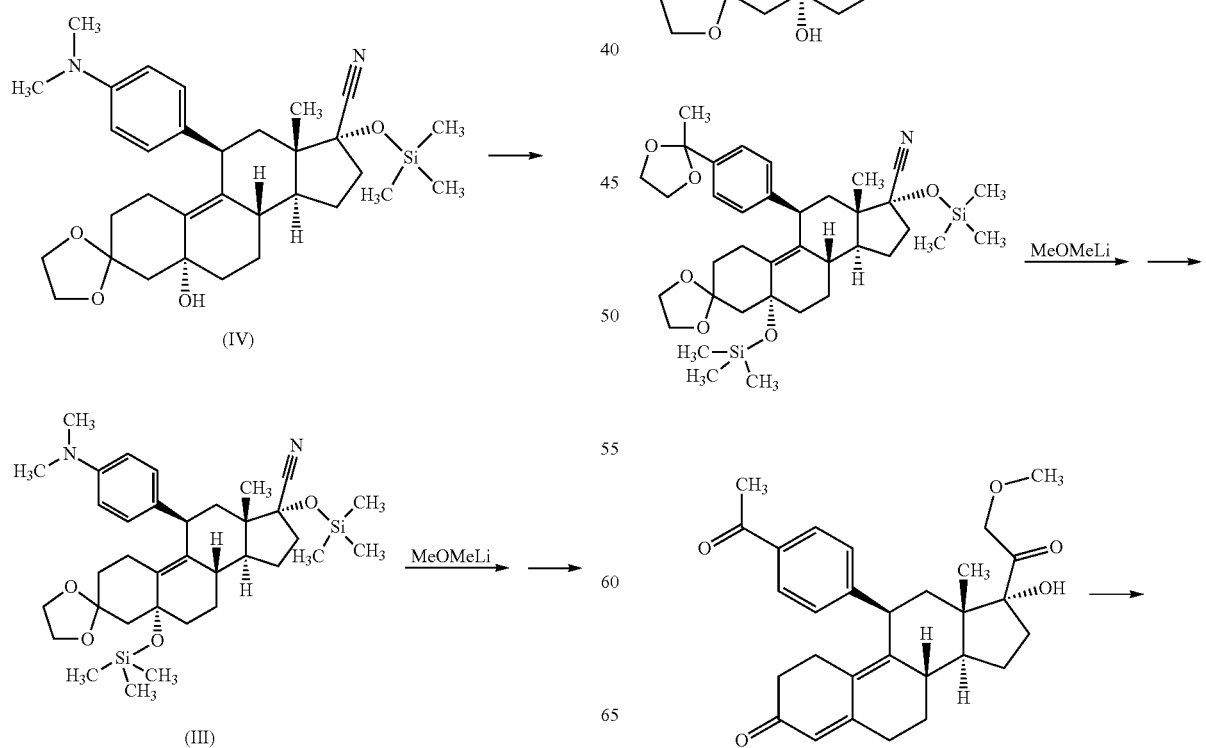

-continued

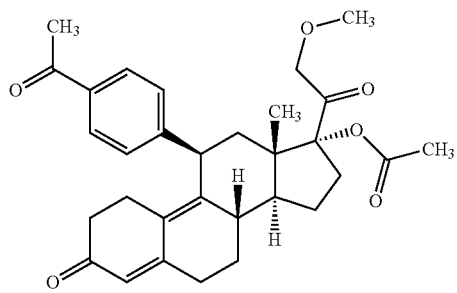

The present invention relates to a new process (Figure 3.) for the synthesis of 21-methoxy-pregnane derivatives of formula (I)

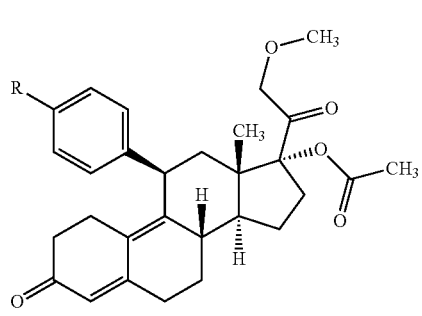

wherein the meaning of R is dimethylamino or acetyl group, to the synthesis of the methoxymethyl lithium reagent used in the process, as well as to the intermediate of formula (III), wherein the meaning of R' is 2-methyl-1,3-dioxolan-2-yl group.

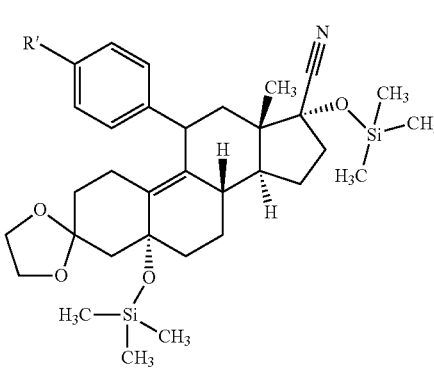

The advantage of the process of our invention is that it has less steps as the known ones described earlier, it is industrially realizable, safe and economical.

According to the process of our invention the hydroxyl group in position 5 of compound of formula (IV),

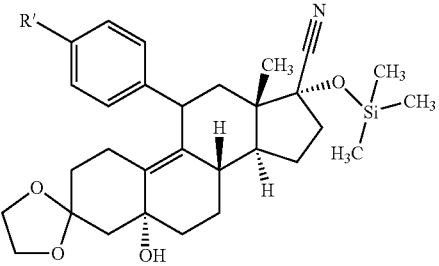

wherein the meaning of R' is 2-methyl-1,3-dioxolan-2-yl group, and synthesized according to method described in patent application No. WO2009001148, is silylated with chloro-trimethylsilane in the presence of imidazole in a halogenated solvent or tetrahydrofuran or toluene, preferably in dichloromethane, at room temperature to yield the compound of formula (III), wherein the meaning of R' is as described above.

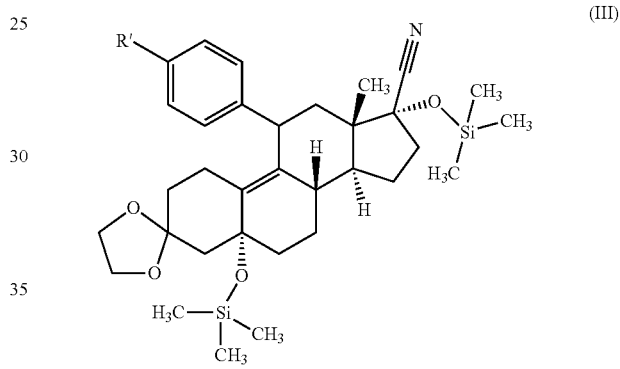

In the next step the methoxymethyl lithium reagent is synthesized. A condensed or conjugated aromatic hydrocarbon in given case substituted with alkyl groups, for example naphthalene, alklylnaphthalene, anthracene, 4,4'-di-tertbutyl-biphenyl, preferably biphenyl, is dissolved in an ether, aliphatic or aromatic hydrocarbon or formaldehyde dialkylacetal type solvent, for example tetrahydrofuran, methyltetrahydrofuran, diethyl ether, diisopropyl ether, methyltertbutyl ether, toluene, dimethoxyethane, diethoxyethane, preferably tetrahydrofuran, and lithium metal is added to the so obtained solution under inert atmosphere. The reaction mixture is vigorously stirred for 0.5-5 hours, preferably for 3 hours, until the lithium is dissolved at 0-20° C., preferably at 5-10° C. Then the solution is cooled to (−78)-(−40°)° C., preferably to −55° C., and methoxymethyl chloride in itself or in a solution of any of the above mentioned solvents is added to the mixture in such a rate as to keep the reaction temperature between (−78)-(−30°)° C., preferably between (−55)-(−40°)° C. The solution of compound of formula (III) or (IV) is added to the so obtained solution at a temperature between (−78)-(−30)° C., preferably between (−55)-(−50)° C. The reaction mixture is stirred at a temperature between (−78)-(−30)° C., preferably between (−48)-(−52)° C. for 0.5-3 hours, preferably for 2 hours.

Then water is added to the reaction mixture in such a rate as to keep the reaction temperature below 0° C., preferably at −10° C. After the addition of water the reaction mixture is vigorously stirred for 10-120 min, preferably for 30 min, while the temperature is allowed to rise to 10-15° C. After settling the phases are separated, the solution containing the protected intermediate is treated with a strong acid, for example hydrochloric acid, sulphuric acid, p-toluenesulphonic acid, perchloric acid, methanesulphonic acid, phosphoric acid, potassium hydrogensulphate, preferably sodium hydrogensulphate, to yield the solution of the compound of formula (II), from which the compound of formula (II),

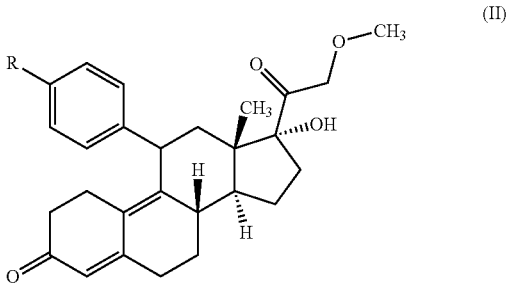

(II)

wherein the meaning of R is dimethylamino or acetyl group, is isolated in a suitable way. The obtained product in given case is purified by chromatography. The hydroxyl group in position 17 is acetylated according to the method described in patent application No. WO2009001148 to yield the final product of formula (I),

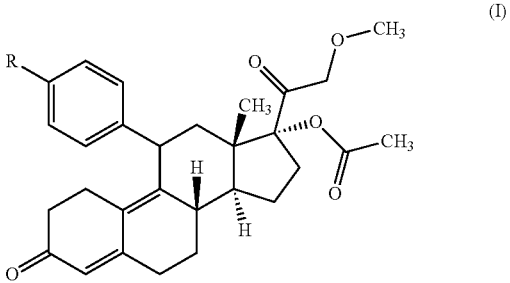

(I)

wherein the meaning of R is as described above.

EXAMPLES

The invention is illustrated by the following not limiting examples.

Example 1

Synthesis of 11β-[(4-dimethylamino)phenyl]17α-hydroxy-21-methoxy-19-norpregna-4,9-dien-3,20-dione :

146.8 g (0.95 M) of biphenyl was dissolved in 920 ml of tetrahydrofuran, the so obtained solution was cooled to 0° C. and 6.0 g (0.84 M) of lithium metal granulate was added under argon atmosphere to the solution. The reaction mixture was vigorously stirred for 3 hours, until the lithium was dissolved at 5-10° C. Then the black solution was cooled to −55° C. During this time 34.6 ml (0.45 M) of methoxymethyl chloride was dissolved in 140 ml of toluene and the so obtained solution was added (about 20 min) to the reaction mixture while keeping the temperature between (−55)-(−40)° C. The so obtained solution of the methoxymethyl lithium reagent was cooled to −55° C. 20.0 g (32.1 mM) of 11β-[4-(dimethylamino)phenyl]-3,3-ethylenedioxy-5α, 17α-bisz-[(trimethylsilyl)oxy]-estr-9-en-17-carbonitrile (Example 5 of WO2009001148) was dissolved in 60 ml of toluene and this solution was added over a period of about 10 min to the methoxymethyl lithium reagent while keeping the temperature of the reaction mixture between (−55)-(−50)° C. Then the reaction mixture was stirred at (−52)-(−48)° C. for 2 hours. After this 240 ml of water was added over a period of about 10 min, the reaction mixture became colourless and warmed to −10° C. After addition of water the reaction mixture was vigorously stirred for 30 min while its temperature was allowed to warm to 10-15° C. The inert atmosphere was kept until the end of the work-up. Stirring was stopped, and after 20 min settling the phases were separated. 150 ml of water was added to the upper organic phase containing the steroid and the mixture was stirred for 5 min, after 20 min settling the phases were separated. Then a 15-20° C. solution of 35 g of sodium hydrogensulphate in 500 ml of water was added over a period of 5-10 min to the upper organic phase containing the steroid. During the hydrolysis the temperature of the reaction mixture was kept at 15-20° C. After 2 hours stirring was stopped, and after settling the phases were separated, the upper organic phase was washed with 2×100 ml of about 10v/v % sulphuric acid, and the water phases were combined. The combined water phases containing the steroid were extracted with 2×100 ml of cyclohexane. Then the water phase was added to a solution of 83.73 g of sodium carbonate in 3 L of water over a period of 10-15 min. The precipitated crystals were filtered off after 30 min stirring, washed several times with water until neutral pH. The product was dried at 40° C. in vacuum oven until constant weight to yield 14.5 g (97.44%) of the title compound.

Overall impurities: 7.15% according to HPLC $^1$H NMR (DMSO-$d_6$, 500 MHz) δ: 6.94-7.06 (m, 2H), 6.62 (s, 2H), 5.66 (s, 1H), 5.37 (s, 1H), 4.51 (d, J=18.4 Hz, 1H), 4.30-4.39 (m, 1H), 4.21 (d, J=18.4 Hz, 1H), 3.26 (s, 3H), 2.82 (s, 6H), 2.75 (dt, J=14.9, 5.1 Hz, 1H), 2.39-2.66 (m, 6H), 2.28-2.38 (m, 1H), 2.07-2.26 (m, 2H), 1.89-2.06 (m, 3H), 1.63-1.75 (m, 1H), 1.32-1.51 (m, 2H), 1.20-1.30 (m, 2H), 0.19 ppm (s, 3H)

$^{13}$C NMR (CDCl$_3$, 125 MHz) δ: 208.8, 197.9, 156.5, 148.2, 146.5, 132.0, 128.1, 127.2, 121.9, 112.5, 88.6, 75.4, 58.3, 50.0, 47.0, 40.1, 38.7, 37.9, 36.5, 36.3, 32.9, 30.3, 27.7, 25.2, 23.4, 15.8 ppm Example 2

Synthesis of 11β-[(4-dimethylamino)phenyl]-17α-hydroxy-21-methoxy-19-norpregna-4,9-dien-3,20-dione :

121.8 g (0.95 M) of naphthalene was dissolved in 920 ml of tetrahydrofuran, the so obtained solution was cooled to 0° C. and 6.0 g (0.84 M) of lithium metal cutted into small pieces was added under argon atmosphere to the solution. The reaction mixture was stirred at 5-10° C. until the lithium was dissolved. Then the black solution was cooled to −55° C. and a solution of 34.6 ml (0.45 M) of chloromethyl methyl ether in 140 ml of toluene was added to the reaction mixture while keeping the temperature below −40° C. The so obtained solution was cooled to −55° C. and a solution of 20.0 g (32.1 mM) of 11β-[4-(dimethylamino)phenyl]-3,3-ethylenedioxy-5α, 17α-bisz-[(trimethylsilyl)oxy]-estr-9-en-17-carbonitrile in 60 ml of toluene was added while keeping the temperature of the reaction mixture below −50° C. Then the reaction mixture was stirred at −50° C. for 3 hours. After this 240 ml of water was added and the reaction mixture was allowed to warm to 20° C. After stirring for 10 min the phases were separated. 500 ml of 0.3 M sulphuric acid was added to the upper organic phase and the mixture was stirred for 2 hours at 20° C. The phases were separated, the upper organic phase was washed with 2×100 ml of 10% sulphuric acid, and the water phases were combined. The combined water phases were extracted with 2×100 ml of cyclohexane. Then the water phase was added to 3 L of 0.3 M sodium carbonate solution. The precipitated crystals were filtered off, washed with water and dried to yield 14.5 g (97.4%) of the title compound.

Example 3

Synthesis of 11β-[(4-dimethylamino)phenyl]-17α-hydroxy-21-methoxy-19-norpregna-4,9-dien-3,20-dione:

146.8 g (0.95 M) of biphenyl was dissolved in 920 ml of tetrahydrofuran, the so obtained solution was cooled to 0° C. and 6.0 g (0.84 M) of lithium metal cutted into small pieces was added under argon atmosphere to the solution. The reaction mixture was stirred at 5-10° C. until the lithium was dissolved. Then the black solution was cooled to −55° C. and a solution of 34.6 ml (0.45 M) of chloromethyl methyl ether in 140 ml of toluene was added to the reaction mixture while keeping the temperature below −40° C. The so obtained solution was cooled to −55° C. and a solution of 16.6 g (30.1 mM) of 11β-[4-(dimethylamino)phenyl]-3,3-ethylenedioxy-5α-hydroxy-17α-[(trimethylsilyl)oxy]-estr-9-en-17-carbonitrile in 120 ml of tetrahydrofuran was added while keeping the temperature of the reaction mixture below −50° C. Then the reaction mixture was stirred at −50° C. for 3 hours. After this 240 ml of water was added and the reaction mixture was allowed to warm to 20° C. After stirring for 10 min the phases were separated. 500 ml of 0.3 M sulphuric acid was added to the upper organic phase and the mixture was stirred for 2 hours at 20° C. The phases were separated, the upper organic phase was washed with 2×100 ml of 10% sulphuric acid, and the water phases were combined. The combined water phases were extracted with 2×100 ml of cyclohexane. Then the water phase was added to 3 L of 0.3 M sodium carbonate solution. The precipitated crystals were filtered off, washed with water and dried to yield 13.3 g (95.2%) of the title compound.

Example 4

Synthesis of 11β-(4-acetylphenyl)-17α-hydroxy-21-methoxy-19-norpregna-4,9-dien-3,20-dione:

146.8 g (0.952 M) of biphenyl was dissolved in 920 ml of tetrahydrofuran, the so obtained solution was cooled to 0° C. and 6.0 g (0.84 M) of lithium metal cutted into small pieces was added under argon atmosphere to the solution. The reaction mixture was stirred at 5-10° C. until the lithium was dissolved. Then the black solution was cooled to −55° C. and a solution of 34.6 ml (0.452 M) of chloromethyl methyl ether in 140 ml of toluene was added to the reaction mixture while keeping the temperature below −40° C. The so obtained solution was cooled to −55° C. and a solution of 21.0 g (31.5 mM) of 3,3-ethylendioxy-11β-[4-(2-methyl-1,3-dioxolan-2-yl)phenyl]-5α,17α-bisz-[(trimethylsilyl)oxy]-estr-9-en-17-carbonitrile in 80 ml of toluene was added while keeping the temperature of the reaction mixture below −50° C. Then the reaction mixture was stirred at −50° C. for 3 hours. After this 240 ml of water was added and the reaction mixture was allowed to warm to 20° C. After stirring for 10 min the phases were separated. 500 ml of 5% sulphuric acid was added to the upper organic phase and the mixture was stirred for 2 hours at 20° C. The phases were separated, and the water phase was extracted with 2×100 ml of toluene. The combined organic phases were washed with 3×100 ml of water and 1×100 ml of brine, dried over anhydrous sodium sulphate and concentrated. The residue was crystallized from methanol in order to remove considerable amount of biphenyl (about 115 g). The methanolic mother liquor was concentrated (about 48 g) and purified by column chromatography using 500 g of silicagel and a 95:5 mixture of dichloromethane and acetone. The fractions containing the product were concentrated and the residue was crystallized from acetone to yield 11.87 g (81.4%) of the title compound.

$^1$H NMR (800 MHz, CDCl$_3$) δ: 7.84-7.90 (m, 2H), 7.25-7.28 (m, 2H), 5.79 (s, 1H), 4.49 (m, 1H), 4.43 (m, 1H), 4.27 (m, 1H), 3.45 (s, 3H), 2.71-2.75 (m, 1H), 2.59-2.65 (m, 3H), 2.57 (s, 3H), 2.53-2.57 (m, 1H), 2.54 (s, 1H), 2.43 (ddd, J=16.3, 11.6, 5.9 Hz, 1H), 2.35 (dt, J=16.3, 5.5 Hz, 1H), 2.24-2.30 (m, 1H), 2.18 (s, 6H), 2.05-2.10 (m, 2H), 1.84-1.91 (m, 1H), 1.61 (ddd, J=15.2, 9.3, 6.2 Hz, 1H), 1.50-1.57 (m, 1H), 1.38 (qd, J=11.7, 6.4 Hz, 1H), 0.34 (s, 3H)

$^{13}$C NMR (201 MHz, CDCl$_3$) δ: 208.2, 199.2, 197.5, 156.2, 150.3, 144.2, 134.9, 129.8, 128.7, 127.0, 123.2, 89.6, 77.0, 59.3, 49.8, 48.3, 40.4, 38.2, 36.7, 36.6, 33.5, 30.9, 30.9, 27.8, 26.5, 25.7, 23.9, 16.3

Example 5

Synthesis of 11β-(4-acetylphenyl)-17α-hydroxy-21-methoxy-19-norpregna-4,9-dien-3,20-dione:

146.8 g (0.952 M) of biphenyl was dissolved in 920 ml of tetrahydrofuran, the so obtained solution was cooled to 0° C. and 6.0 g (0.84 M) of lithium metal cutted into small pieces was added under argon atmosphere to the solution. The reaction mixture was stirred at 5-10° C. until the lithium was dissolved. Then the black solution was cooled to −55° C. and a solution of 34.6 ml (0.452 M) of chloromethyl methyl ether in 140 ml of toluene was added to the reaction mixture while keeping the temperature below −40° C. The so obtained solution was cooled to −55° C. and a solution of 17.8 g (30.0 mM) of 3,3-ethylendioxy-11β-[4-(2-methyl-1,3-dioxolan-2-yl)phenyl]-5α-hydroxy-17α-[(trimethylsilyl)oxy]-estr-9-en-17-carbonitrile in 80 ml of toluene was added while keeping the temperature of the reaction mixture below −50° C. Then the reaction mixture was stirred at −50° C. for 3 hours. After this 240 ml of water was added and the reaction mixture was allowed to warm to 20° C. After stirring for 10 min the phases were separated. 500 ml of 5% sulphuric acid was added to the upper organic phase and the mixture was stirred for 2 hours at 20° C. The phases were separated, and the water phase was extracted with 2×100 ml of toluene. The combined organic phases were washed with 3×100 ml of water and 1×100 ml of brine, dried over anhydrous sodium sulphate and concentrated. The residue was crystallized from methanol in order to remove considerable amount of biphenyl (about 115 g). The methanolic mother liquor was concentrated (about 48 g) and purified by column chromatography using 500 g of silicagel and a 95:5 mixture of dichloromethane and acetone. The fractions containing the product were concentrated and the residue was crystallized from acetone to yield 10.5 g (75.7%) of the title compound.

Example 6

Synthesis of 3,3-ethylendioxy-11β-[4-(2-methyl-1, 3-dioxolan-2-yl)-phenyl]-5α,17α-bis[(trimethylsilyl) oxy]-estr-9-en-17-carbonitrile :

25 g (41.68 mM) of 3,3-ethylendioxy-11β-[4-(2-methyl-1,3-dioxolan-2-yl)phenyl]-5α-hydroxy-17α-[(trimethylsilyl)oxy]-estr-9-en-17-carbonitrile (Example 25 of WO174840) was dissolved in 125 ml of dichloromethane and 5 g of imidazole was added to the solution. 8.4 ml of chlorotrimethylsilane was added dropwise to the so obtained solution at 20° C. The reaction mixture was stirred at 20-25° C. for 1 hour, then diluted with 70 ml of dichloromethane and 70 ml of water was added. After vigorously stirring for 10 min the phases were separated, the organic phase was washed with 2×50 ml of water, dried over anhydrous sodium sulphate and concentrated. The residue was crystallized from methanol to yield 22.2 g (80.0%) of the title compound.

$^1$H NMR (800 MHz, CDCl$_3$) δ: 7.34 (m, 2H), 7.16 (m, 2H), 4.33 (m, 1H), 3.99-4.05 (m, 2H), 3.96 (m, 1H), 3.88-3.94 (m, 1H), 3.83-3.88 (m, 1H), 3.77-3.83 (m, 2H), 3.73-3.77 (m, 1H), 2.37-2.46 (m, 1H), 2.24-2.35 (m, 3H), 2.21 (dd, J=14.4, 2.6 Hz, 1H), 2.12-2.18 (m, 1H), 2.04 (m, 1H), 2.08 (dd J=14.4, 0.9 Hz, 1H) 1.97 (ddd, J=14.8, 9.1, 5.5 Hz, 1H), 1.75-1.88 (m, 2H), 1.65-1.73 (m, 4H), 1.64 (s, 3H), 1.47-1.57 (m, 1H), 1.34 (m, 1H), 1.20 (td, J=12.8, 4.0 Hz, 1H), 0.48 (s, 3H), 0.26 (s, 9H), 0.18 (s, 9H)

$^{13}$C NMR (201 MHz, CDCl$_3$) δ: 145.9, 140.3, 136.2, 132.6, 126.9, 125.1, 120.9, 108.8, 108.4, 78.8, 73.5, 64.5, 64.5, 64.4, 63.4, 50.1, 49.0, 47.2, 38.9, 38.6, 38.6, 38.5, 35.6, 34.9, 27.4, 24.6, 24.5, 23.5, 17.0, 2.6, 1.1

Example 7

Synthesis of 17α-acetoxy-11β-[(4-dimethylamino) phenyl]-21-methoxy-19-norpregna-4,9-dien-3,20-dione (CDB-4124)

21 ml (222 mM) of acetic anhydride was cooled to (−25)-(−20)° C. and 2.8 ml (33 mM) of 70% perchloric acid was added while keeping the temperature below −15° C. A solution of 7 g (15.1 mM) of 11β-[(4-dimethylamino)phenyl]-17α-hydroxy-21-methoxy-19-norpregna-4,9-dien-3, 20-dione in 32 ml of dichloromethane was added to the acylating mixture at (−25)-(−20)° C. After the addition was finished the reaction mixture was stirred at (−25)-(−20)° C. for 30 min, then it was added to a cooled mixture—0-(−5)° C.—of 35 ml of 25% aqueous ammonia and 55 ml of water. The so obtained mixture was diluted with 30 ml of dichloromethane, and stirred at 20-25° C. for 30 min. The phases were separated, the organic phase was washed with 2×25 ml of water, then dried over sodium sulphate, filtered and concentrated. The obtained crude product (7.5 g) was purified by column chromatography using a 1:1 mixture of cyclohexane and ethyl acetate. The fractions containing the product were concentrated and the residue was crystallized from methanol to yield 4.9 g (64%) of the title compound.

Melting point: 201-204° C.

NMR: $^1$H NMR (500 MHz, CDCl$_3$ (TMS), δ (ppm)): 0.40 (3H, s, 18-CH$_3$); 2.10 (3H, s. O—CO—CH$_3$); 2.90 (6H, s, N—CH$_3$); 3.41 (3H, s, O—CH$_3$); 4.09 (1H, d, H$_x$-21); 4.38 (1H, m, H-11); 4.29 (1H, d, H$_y$-21); 5.77 (1H, br, H-4); 6.62 (2H, m, H-3' & H-5'); 6.96 (2H, m, H-2' & H-6')

$^{13}$C NMR (125 MHz, CDCl$_3$ (IMS), δ (ppm)): 15.6 (C-18); 21.1 (O—CO—CH$_3$); (39.3 (C-11); 40.6 (N—CH$_3$); 59.4 (O—CH$_3$); 76.0 (C-21); 93.9 (C-17); 112.8 (C-3' & C-5'); 123.0 (C-4); 127.3 (C-2' & C-6'); 129.4 (C-10); 131.3 (C-1'); 145.5 (C-9); 148.7 (C-4'); 156.4 (C-5); 170.7 (O—CO—CH$_3$); 199.4 (C-3); 202.7 (C-20)

Example 8

Synthesis of 17α-acetoxy-11β-(4-acetylphenyl)-21-methoxy-19-norpregna-4,9-dien-3,20-dione (CDB-4239):

25 ml (264 mM) of acetic anhydride was cooled to (−25)-(−20)° C. and 3.4 ml (40 mM) of 70% perchloric acid was added while keeping the temperature below −15° C. A solution of 8.5 g (18.4 mM) of 11β-(4-acetylphenyl)-17α-hydroxy-21-methoxy-19-norpregna-4,9-dien-3,20-dione in 90 ml of dichloromethane was added to the acylating mixture at (−25)-(−20)° C. After the addition was finished the reaction mixture was stirred at (−25)-(−20)° C. for 30 min, then it was added to a cooled mixture—0-(−5)° C.—of 42 ml of 25% aqueous ammonia and 70 ml of water. The reaction mixture was stirred at 20-25° C. for 30 min, then the phases were separated, the organic phase was washed with 2×30 ml of water, dried over sodium sulphate, filtered and concentrated in vacuum. The obtained crude product (8.5 g) was purified by column chromatography using a 1:1 mixture of cyclohexane and ethyl acetate. The fractions containing the product were concentrated and the residue was crystallized from methanol to yield 6.8 g (73%) of the title compound.

Melting point: 110-116° C.

The invention claimed is:

1. Process for the synthesis of compound of formula (I)

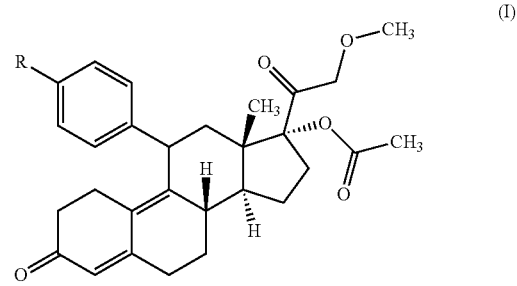

(I)

wherein the meaning of R is dimethylamino or acetyl group, characterized by a) reacting the compound of formula (III) or (IV),

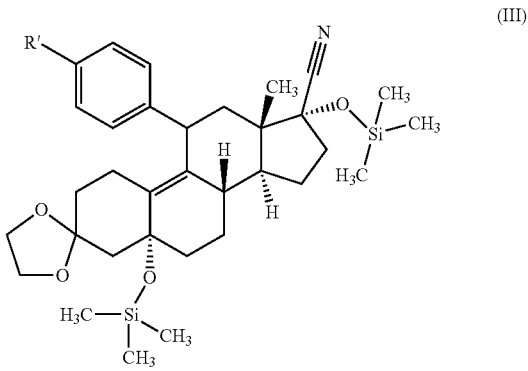

(III)

-continued

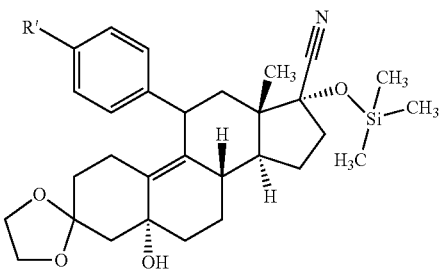

(IV)

wherein the meaning of R' is dimethylamino or 2-methyl-1,3-dioxolan-2-yl group,
with methoxymethyl lithium,
b) removing the protective groups of the so obtained intermediate, and
c) acylating the hydroxyl group in position 17 of the so obtained compound of formula (II)

(II)

2. The process according to claim 1, characterized by synthesizing the methoxymethyl lithium reagent the following way:
 a) an isolated or a condensed ring aromatic hydrocarbon is dissolved in an ether type solvent,
 b) lithium metal is added to the so obtained solution under inert atmosphere,
 c) the mixture is stirred at 0-20° C. until lithium is dissolved,
 d) the mixture is cooled to (−78)-(−40)° C. and methoxymethyl chloride is added.

3. The process according to claim 2, characterized by using naphthalene or biphenyl as an isolated or a condensed ring aromatic hydrocarbon.

4. The process according to claim 2, characterized by using tetrahydrofuran as an ether type solvent.

5. The process according to claim 2, characterized by carrying out the reaction of step c) of claim 2 at a temperature between 5-10° C.

6. The process according to claim 2, characterized by carrying out the reaction of step d) of claim 2 at a temperature of −55° C.

7. The process according to claim 1 characterized by removing the protective groups by acid hydrolysis and dehydration.

8. The process according to claim 1, characterized by synthesizing the methoxymethyl lithium reagent in situ.

9. The process according to claim 1, wherein R and R' are dimethylamino.

* * * * *